(12) United States Patent
Jinotti

(10) Patent No.: US 6,427,691 B1
(45) Date of Patent: Aug. 6, 2002

(54) MEDICAL VALVE

(76) Inventor: Walter Jinotti, 459 Somerset St., New Brunswick, NJ (US) 08873

( * ) Notice: Subject to any disclaimer, the term of this patent is extended or adjusted under 35 U.S.C. 154(b) by 0 days.

(21) Appl. No.: 09/350,157

(22) Filed: Jul. 9, 1999

(51) Int. Cl.$^7$ ................................................ A62B 9/02
(52) U.S. Cl. ........................... 128/205.24; 128/205.19
(58) Field of Search ..................... 128/205.24, 205.18, 128/205.19, 207.14, 207.15, 207.16, 912; 137/907, 908

(56) References Cited

U.S. PATENT DOCUMENTS

| | | | | |
|---|---|---|---|---|
| 3,918,447 A | * | 11/1975 | Inkster et al. | 128/145.8 |
| 4,193,406 A | * | 3/1980 | Jinotti | 128/205.24 |
| 4,333,451 A | * | 6/1982 | Paluch | 128/205.12 |
| 4,437,461 A | * | 3/1984 | Greenberg | 128/205.24 |
| 4,572,175 A | * | 2/1986 | Flynn | 128/205.24 |
| 4,674,496 A | * | 6/1987 | Svadjian et al. | 128/207.16 |
| 4,699,137 A | * | 10/1987 | Schroeder | 128/205.24 |
| 4,705,073 A | * | 11/1987 | Beck | 128/205.24 |
| 5,088,486 A | * | 2/1992 | Jinotti | 128/207.14 |
| 5,165,398 A | * | 11/1992 | Bird | 128/205.24 |
| 5,191,881 A | * | 3/1993 | Beck | 128/205.24 |
| 5,245,996 A | * | 9/1993 | Manicom | 128/205.24 |
| 5,275,153 A | * | 1/1994 | Kay | 128/205.24 |
| 5,309,904 A | * | 5/1994 | Beck | 128/205.24 |
| 5,400,779 A | * | 3/1995 | DeResende | 128/205.24 |
| 5,511,545 A | * | 4/1996 | Jinotti | 128/205.24 |
| 5,664,564 A | * | 9/1997 | Palmer | 128/205.24 |
| 5,735,271 A | * | 4/1998 | Lorenzen et al. | 128/205.24 |
| 5,738,091 A | * | 4/1998 | Kee et al. | 128/205.24 |
| 5,746,199 A | * | 5/1998 | Bayron et al. | 128/205.24 |
| 6,102,038 A | * | 8/2000 | DeVries | 128/205.24 |
| 6,123,674 A | * | 9/2000 | Rich | 128/205.24 |

FOREIGN PATENT DOCUMENTS

EP 0347026 * 12/1989 ............ 128/205.24

* cited by examiner

Primary Examiner—John G. Weiss
Assistant Examiner—Teena Mitchell
(74) Attorney, Agent, or Firm—Robert A. Green

(57) ABSTRACT

The disclosure is of a medical valve for handling oxygen and suction and including a suction flow path in which there is a means for throttling down the flow to a level at which there are no, possibly damaging, surges.

2 Claims, 1 Drawing Sheet

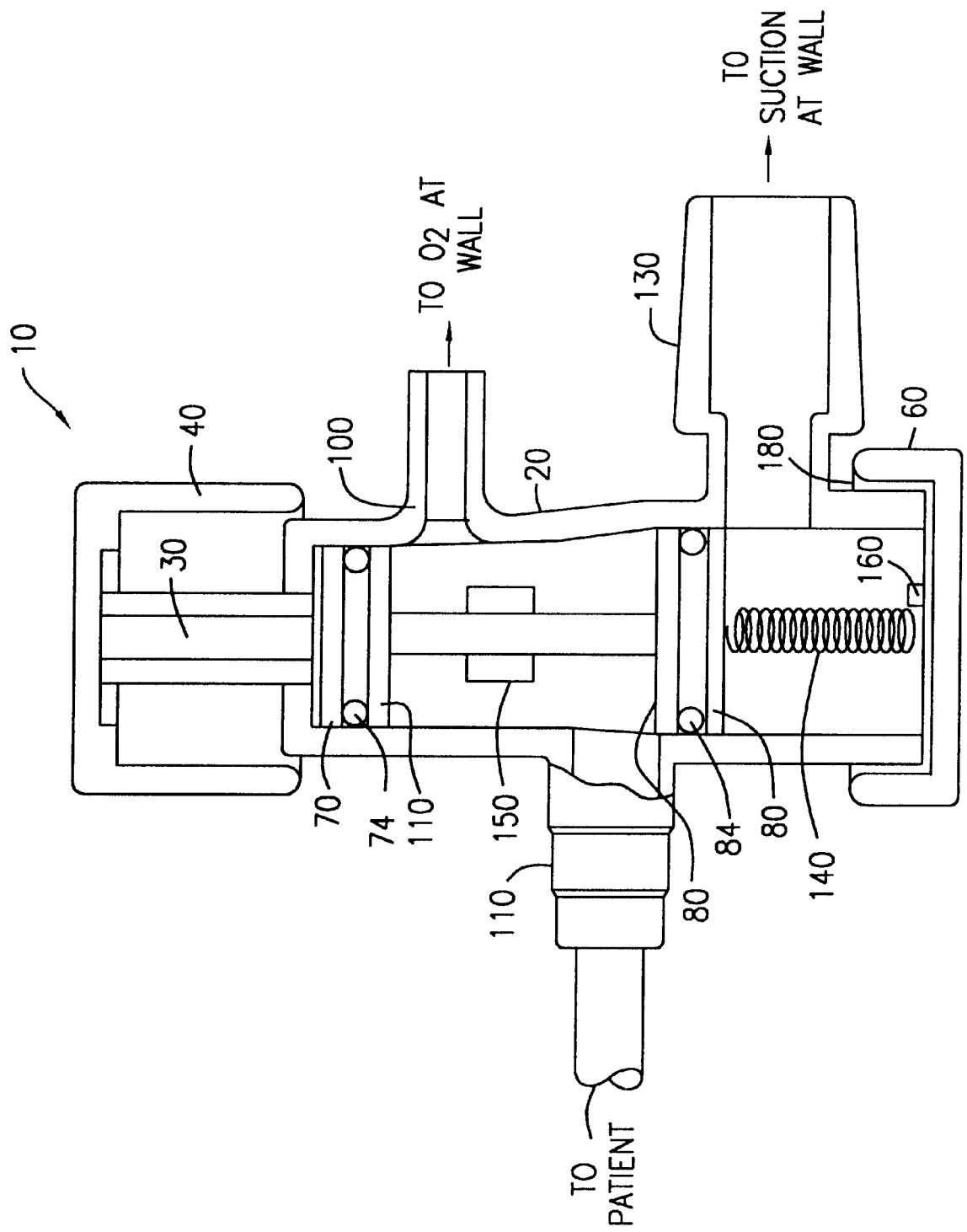

MEDICAL VALVE

BACKGROUND OF THE INVENTION

The present invention relates to apparatus for treating a medical patient with oxygen or suction or both. Some apparatus is known for feeding oxygen or suction or both to a patient but none is known in which the pressure of gas can be controlled and the patient can be so well protected from a surge of pressure.

SUMMARY OF THE INVENTION

The present invention can be used to feed gases while maintaining tight control on gas pressure surges to which the patient might be subjected.

DESCRIPTION OF THE DRAWINGS

The drawing is a sectional view through the control valve of the invention.

DESCRIPTION OF THE INVENTION

Referring to the drawing, the control valve of the invention 10 includes a generally cylindrical housing 20 of metal, plastic or the like suitable for the purposes of the invention. The housing includes a piston 30 of metal or other suitable material slidably disposed therein. The housing includes a cap 40 at its upper end and a cap 60 at its lower end The upper cap is slidable up and down on the upper end of the housing.

The piston carries, near its upper end, an assembly of plates 70 spaced apart by an O-ring 74. This assembly slides inside the cylinder in gas-tight engagement with the inner wall of the housing cylinder. In the up position of the plunger, the The assembly of plates 70 engages the upper end wall of the cylinder as a stop. The upper cap is slidable on the housing.

The piston also carries an assembly of plates 80 and O-ring 84 positioned as described below.

The housing 20 carries the following tubes. An oxygen tube 100 is secured to the housing near the upper end thereof below the assembly of plates 70 (when the plunger is up) and this tube is connected to a source of oxygen at a wall mounting. Beneath this tube is a patient tube 110 which extends by a catheter 120 to a patient. Finally, a suction tube 130 is secured near the lower end of the housing beneath the patient tube and extends to a source of suction at the wall. The lower set of plates 80 is positioned just above the suction tube 130 when the plunger is up.

As seen in the drawing, the piston is in the up position in which the tube 100 from wall oxygen has oxygen flow from the wall around the piston to the outlet 100 to the patient. At this time, the lower assembly of plates causes suction to flow to atmosphere through the slits in the lower cap. If the cap is pressed downwardly, the piston moves to the position in which the oxygen tube 100 is blocked by the plate assembly 70 and the outlet to the patient is open and the lower plates are beneath the suction line 130 as shown in dash lines. Thus there can be flow of suction from the wall to the patient.

According the invention, the outer wall of the piston is provided with an enlargement 150 which is called a throttle plate. This enlargement is of such size that when the plunger is down, the throttle plate lies in the path from the patient to the source of suction. The throttle plate does not block this path but throttles down the velocity of the flow of suction where surges are prevented.

In operation of the valve 10, when the piston is raised, oxygen flows from the wall into tube 190 and through the piston and out the tube to a patient. At this time, the assembly of plates 150 blocks a suction path and causes suction to flow to atmosphere through the slots in the bottom cap 170.

When the plunger is pushed down, the plate 150 lies below the suction line and the throttle lies across the opening in the tube and air flow from the wall suction source in the patient tube is reduced in velocity or intensity and controlled suction is achieved. This prevents suction surges and provide safety for the patient.

What is claimed is:

1. Apparatus for handling medical gases comprising a tubular housing having an upper end and a lower end, a slidable assembly in said housing for blocking off selected portions of said housing at selected times, a vertical shaft in said housing and extending from above the upper end thereof to the lower end thereof, a spring secured beneath said lower end or said shaft and said slidable assembly to limit the downward movement thereof, an upper operating cap secured to the upper end of said shaft outside said housing adjacent to the upper end thereof and manipulable by an operator to slide said vertical shaft up and down, a lower operating cap secured to the lower end of said housing, there being air vent holes in said lower cap to permit the flow of gas therethrough from atmosphere, a first side tube secured to said housing near an upper end thereof and adapted to be connected to a source of oxygen, a second tube secured to said housing near a lower end thereof and adapted to be coupled to a patient, and a third tube secured to the lower end of said housing just above said lower cap, said third tube communicating with said vent holes in said lower cap and with a source of suction.

2. The apparatus defined in claim 1 not including a plate secured to said vertical shaft and operating as a throttle plate to control the flow of gas therethrough.

* * * * *